United States Patent [19]
Dorziotis et al.

[11] Patent Number: 6,080,876
[45] Date of Patent: Jun. 27, 2000

[54] PROCESS FOR MAKING PHENYL HETEROCYCLES USEFUL AS COX-2 INHIBITORS

[75] Inventors: Ilias Dorziotis, Bridgewater; Ioannis Houpis, Plainfield, both of N.J.; Kan K. Eng, Yonkers, N.Y.

[73] Assignee: Merck & Co., Inc., Rahway, N.J.

[21] Appl. No.: 09/160,203

[22] Filed: Sep. 17, 1998

Related U.S. Application Data

[60] Provisional application No. 60/063,365, Oct. 29, 1997.

[51] Int. Cl.[7] ................... C07D 307/58; C07D 307/60
[52] U.S. Cl. ............................................. 549/319
[58] Field of Search ............................... 549/319

[56] References Cited

U.S. PATENT DOCUMENTS

| | | | |
|---|---|---|---|
| 5,474,995 | 12/1995 | Ducharme et al. | 514/241 |
| 5,480,568 | 1/1996 | Pawloski et al. | 252/46.7 |
| 5,883,267 | 3/1999 | Rossen et al. | 549/319 |

FOREIGN PATENT DOCUMENTS

| | | |
|---|---|---|
| WO 91/16055 | 10/1991 | WIPO . |
| WO 95/00501 | 1/1995 | WIPO . |
| WO 95/05376 | 2/1995 | WIPO . |
| Wo 96/19469 | 6/1996 | WIPO . |

*Primary Examiner*—Bernard Dentz
*Attorney, Agent, or Firm*—Richard C. Billups; Elliot Korsen; David L. Rose

[57] ABSTRACT

The invention encompasses a process for making compounds of Formula I useful in the treatment of cyclooxygenase-2 mediated diseases.

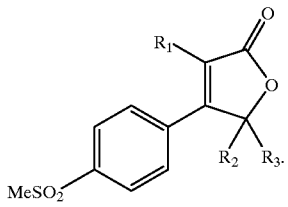

I

18 Claims, No Drawings

PROCESS FOR MAKING PHENYL HETEROCYCLES USEFUL AS COX-2 INHIBITORS

CROSS REFERENCE TO RELATED APPLICATIONS

This application is a non-provisional application related to U.S. application Ser. No.60/063,365, filed on Oct. 29, 1997 priority of which is claimed hereunder.

BACKGROUND OF THE INVENTION

This invention concerns a process for making certain anti-inflammatory compounds. In particular, the application concerns a process for making compounds of formula I, as disclosed hereinunder, which are potent cyclooxygenase-2 inhibitors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastro-intestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 94/15932 published Jul. 21, 1994 discloses a multi-step method of making bi-aryl furans via bi-aryl lactones, which method utilizes a keto-ester internal cyclization to the lactone. Co-pending U.S. patent application Ser. No. 08/851, 962 discloses an improved process for preparing these compounds, however, the process disclosed involves the formation of an undesirable bromosulfone intermediate.

SUMMARY OF THE INVENTION

The invention encompasses an improved process for making compounds of Formula I useful in the treatment of inflammation and other cyclooxygenase-2 mediated diseases.

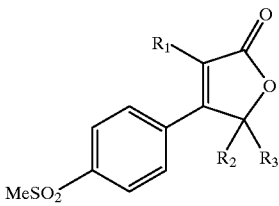

I

In particular, the invention encompasses an improved process for making compound 1 of the formula

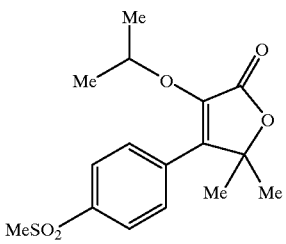

1 which has been found to be useful in the treatment of inflammation and other cyclooxygenase-2 mediated diseases.

DETAILED DESCRIPTION OF THE INVENTION

In one aspect, the invention encompasses a process for making compounds of Formula I useful in the treatment of inflammation and other cyclooxygenase-2 mediated diseases

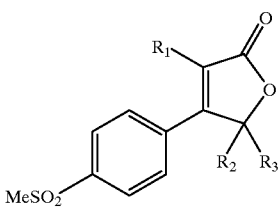

I wherein
  $R_1$ is selected from the group consisting of
    (a) linear or branched $C_{1-6}$alkyl,
    (b) linear or branched $C_{1-6}$alkoxy,
    (c) mono-, di- or tri-substituted phenyl or naphthyl wherein the substituents are selected from the group consisting of
      (1) hydrogen,
      (2) halo,
      (3) $C_{1-3}$alkoxy,
      (4) CN,
      (5) $C_{1-3}$fluoroalkyl
      (6) $C_{1-3}$alkyl,
      (7) —$CO_2H$,
  $R_2$ and $R_3$ are independently selected from the group consisting of
    (1) linear or branched $C_{1-6}$alkyl, or
    (2) aryl, optionally substituted with $R_1$, the process comprising:
(a) reacting thioanisole of the formula

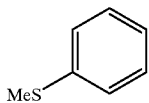

in a non-reactive solvent and in the presence of a Lewis Acid, with an acyl chloride

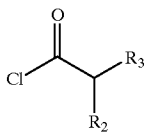

to yield compound III

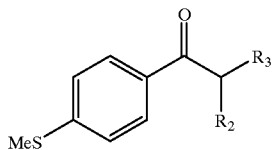

III

For purposes of this specification, non-reactive solvents include halocarbon and polyhalocarbon solvents such as mono or di-halo $C_{1-4}$ alkyl including dichloromethane; aromatic solvents such as nitrobenzene, or halogenated aromatics and $C_{6-10}$ linear, branched or cyclic hydrocarbon solvent including hexane, cyclohexane or methylcyclohexane or $CS_2$. For this step, the non-reactive solvents are preferably cyclohexane or ortho dichlorobenzene. Suitable Lewis Acids include but are not limited to $AlCl_3$, $FeCl_3$, $TiCl_4$ and $SnCl_4$.

The molar ratio of thioanisole compound II to the acyl chloride may typically be varied from 1:1.5 to 1.5:1; preferably 1:1 to 1.5. Excess alkyl chloride is typically used. The preferred acyl chloride has been found to be isobutyryl chloride. Similarly, the molar ratio of thioanisole compound II to Lewis Acid may typically be varied from 1:1.5 to 1.5:1. Preferably the molar ratio of thioanisole compound II to Lewis Acid is 1:1 to 1.5. The reaction step may conveniently be conducted at a temperature range of about 0 to about 25° C.; preferably about 5 to about 15° C. and is allowed to proceed until substantially complete in from about 30 min. to about 4 hours; typically about 1 to about 2 hours.

The reaction is preferably conducted is the absence of moisture, preferable under nitrogen.

(b) oxidizing compound III in a non-reactive solvent (as defined above), with an oxidizing agent, optionally in the presence of a suitable catalyst to yield compound IV

IV

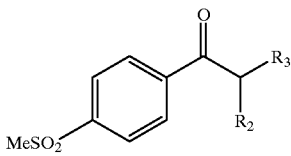

The oxidation may be accomplished by a number of means available in the art. See, for example *Can. J. Chem.*
59,720 (1981), *Can. J. Chem.* 60, 618 (1982), *J. Chem. Soc.* (C) 1969, 233, *J. Org. Chem.,* 28, 1140 (1963), *Org. Prep. Proceed. Int,* 13, 137 (1981), *J. Org. Chem.,* 50, 1544, (1985), *Chem. Ber.,* 119, 269, (1986), and *Synthesis,* 1015, 1987. We have found catalyzed oxidation with hydrogen peroxide to be surprisingly superior in that undesired side-reaction oxidations are minimized and environmental impact and removal of side products are good, as water is the by product.

Suitable catalysts include sodium tungstate di-hydrate and tungstic acid.

Typically the molar ratio of compound III to oxidizing agent should be approximately 1 to 2:4, that is excess oxidizing agent is preferred. The addition of hydrogen peroxide may be conducted at a temperature range of about 0 to about 70° C.; preferably about 10 to about 65° C. and is allowed to proceed until substantially complete in from about 1 to about 5 hours; typically about 2 to about 4 hours.

(c) reacting compound IV in an alkanol solvent with NBS and $K_2CO_3$ to yield the epoxide compound of formula V

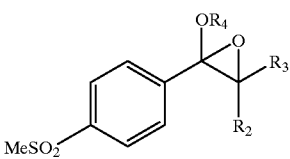

V where $R_4$ is selected from the group consisting of
(1) linear or branched $C_{1-6}$alkyl, or
(2) aryl, optionally substituted with $R_1$.

For purposes of this specification, the alkanol solvent includes, but is not limited to ethyl alcohol. Typically the molar ratio of compound IV to NBS may conveniently be varied from 1.5:1 to 1:1.5; preferably 1:1 to 1.2. Excess NBS is typically used. The reaction step may be conducted at a temperature range of about 0 to about 80° C.; preferably about 10 to about 70° C., and is allowed to proceed until substantially complete in from about 2 to about 20 hours; typically about 8 to about 16 hours.

(d) reacting compound V in a non-reactive solvent such as toluene with an alkyl or alkoxy acetic acid VI

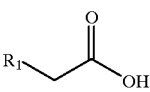

to yield a compound of formula VII

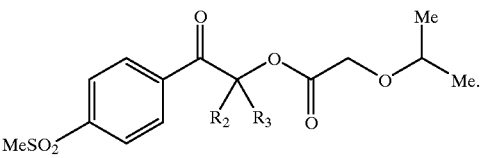

Isopropoxyacetic acid 6, the preferred alkyloxyacetic acid of the formula,

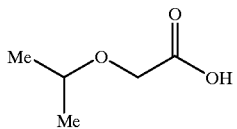

was prepared by addition of sodium chloroacetate to a solution of sodium isopropoxide in isopropanol, generated by reaction of sodium hydroxide and isopropanol. The reaction is typically complete after reflux for 4–5 h. The reaction is quenched by addition of water and isopropanol is removed under vacuum. The aqueous solution is acidified and saturated with sodium chloride and isopropoxyacetic acid is extracted into methyl t-butyl ether. Typically, the reaction yield is only moderate (~75%) due to hydrolysis. Regarding the preparation of Isopropoxyacetic acid, see also J. Chem. Soc.(c) 1969, 2698; J. Am. Chem. Soc. 1949, 71, 3372; and J. Chem Soc. Perkin. Trans. I 1983, 2479.

(e) reacting compound VII in an aprotic solvent with a strong base to yield a compound of formula I.

With regard to the cyclization, a strong base is required to prevent a cessation of the reaction after formation of the ester (VI). Thus, for purposes of this specification the strong base shall be defined to include 1,8-Diazabicyclo[5.4.0]undec-7-ene (DBU), 1,4-diazabicyclo [2.2.2]octane (DABCO) and 1,5diazabicyclo[4.3.0]non-5-ene (DBN). For purposes of this specification the water scavenger shall be defined to include Esters of trifluoroacetic acid, such as isopropyl trifluoroacetate, esters of trichloroacetic acid and esters of alkyl or aryl sulfonic acid. Aprotic solvents shall be defined to include acetonitrile, N,N-dimethyl-formamide, methyl sulfoxide, propionitrile and nitromethane. Dehydration is accomplished by heating (refluxing). The molar ratio of ester to strong base typically about 1:1 to 1: 2, with 1:1.5 preferred. The molar ratio of ester to water scavenger is typically 1:1 to 1:2, with 1:1.2 preferred. The reaction is allowed to proceed at about 0 to about 25° until substantially complete in about 1 to about 14 hours.

Bases such as potassium bis(trimethylsilyl)amide or Lithium diisopropylamide (LDA) cause the cleavage of the ester, possibly through ketene formation and are therefore less preferred. A significant amount of the above mentioned alcohol side product was formed together with several unidentified side-products, which were likely derived from the ketene. Cyclization under acidic conditions fail since ester cleavage is consistently observed as the major reaction.

In a second aspect, the invention encompasses a process for making compounds of Formula I useful in the treatment of inflammation and other cyclooxygenase-2 mediated diseases

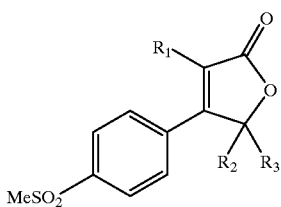

wherein
$R_1$ is selected from the group consisting of
  (a) linear or branched $C_{1-6}$alkyl,
  (b) linear or branched $C_{1-6}$alkoxy,
  (c) mono-, di- or tri-substituted phenyl or naphthyl wherein the substituents are selected from the group consisting of
    (1) hydrogen,
    (2) halo,
    (3) $C_{1-3}$alkoxy,
    (4) CN,
    (5) $C_{1-3}$fluoroalkyl
    (6) $C_{1-3}$alkyl,
    (7) -$CO_2H$,
$R_2$ and $R_3$ are independently selected from the group consisting of
  (1) linear or branched $C_{1-6}$alkyl, or
  (2) aryl, optionally substituted with $R_1$,
the process comprising:
  (e) reacting compound VII

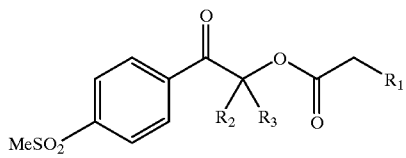

in an aprotic solvent with a strong base and dehydrating in the presence of a water scavenger to yield a compound of formula I

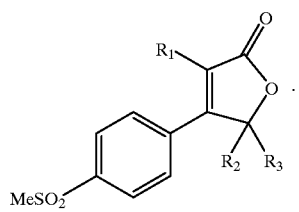

In a preferred embodiment of the invention, there is disclosed a process for making compound 1 of the formula

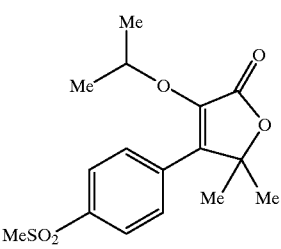

comprising
  (a) reacting thioanisole of the formula

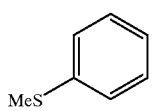

in a non-reactive solvent and in the presence of a Lewis Acid, with isobutyryl chloride

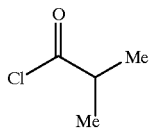

to yield compound 3

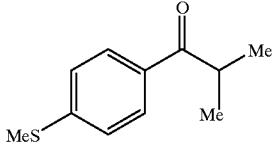

3

(b) oxidizing compound 3 in a non-reactive solvent with an oxidizing agent, optionally in the presence of a suitable catalyst, to yield compound 4

4

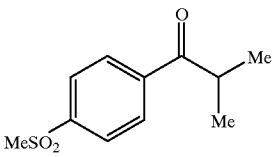

(c) reacting compound 4 in an alkanol solvent with NBS and $K_2CO_3$ to yield the epoxide compound of formula 5

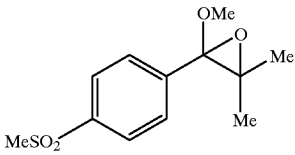

5

(d) reacting compound 5 in a non-reactive solvent with isopropoxyacetic acid 6

6

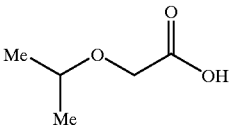

to yield a compound of formula 7

7

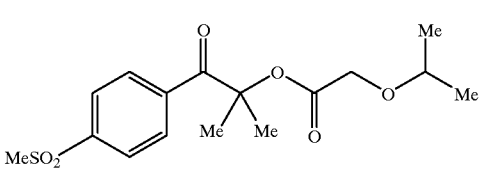

(e) reacting compound 7 in an aprotic solvent with a strong base and dehydrating in the presence of a water scavenger to yield Compound 1.

In another preferred embodiment of the invention, there is disclosed a process for making compound 1 of the formula

1

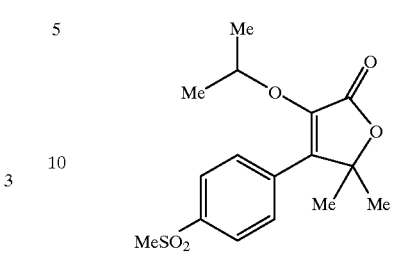

comprising (e) reacting compound 7

7

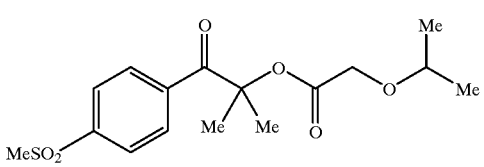

in an aprotic solvent with a strong base and dehydrating in the presence of a water scavenger to yield Compound 1.

The invention is further illustrated in the following steps wherein preferred reactants are shown to more clearly demonstrate the process disclosed. In the scheme, $R_2$, $R_3$ and $R_4$ are shown as methyl and $R_1$ is O—CH(CH$_3$)2.

SCHEME 1

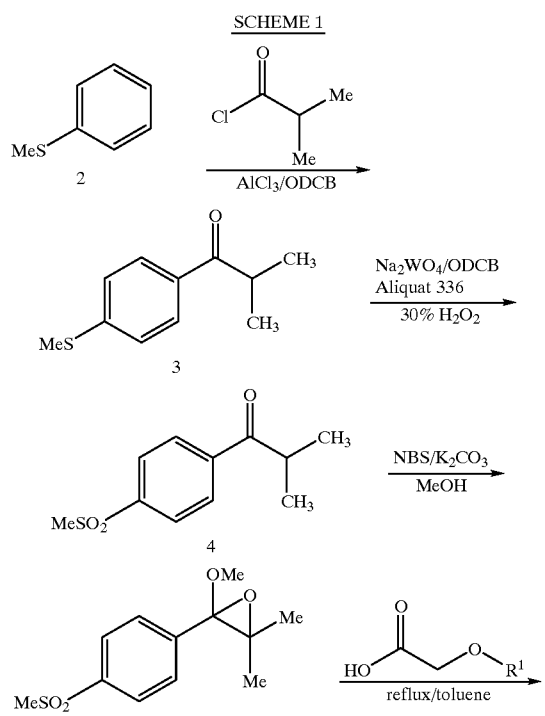

-continued

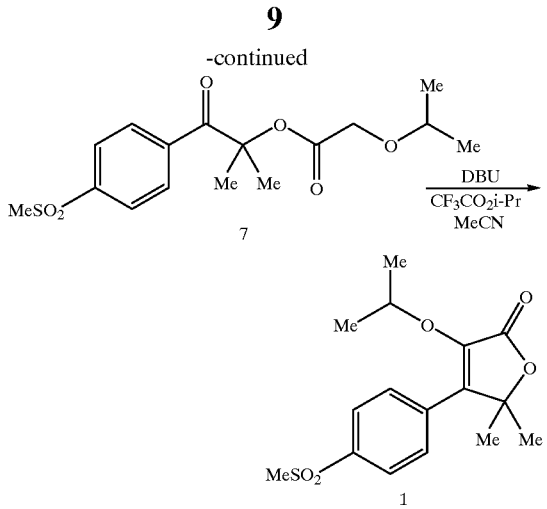

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

By virtue of its high cyclooxygenase-2 (COX-2) activity and/or its selectivity for cyclooxygenase-2 over cyclooxygenase-1 (COX-1) as defined above, compounds of formula I and formula Ia will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Compounds of the present invention are inhibitors of cyclooxygenase-2 and are thereby useful in the treatment of cyclo-oxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 μM. By way of comparison, Ibuprofen has an IC50 for COX-2 of 1 μM, and Indomethacin has an IC50 for COX-2 of approximately 100 nM.

For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The invention will now be illustrated by the following non-limiting examples in which, unless stated otherwise:

(i) All operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) or High Pressure Liquid Chromatography (HPLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

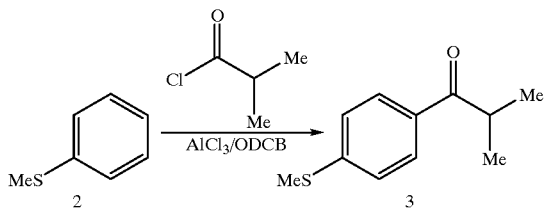

| Material | MW | amount | mmol | equiv. |
|---|---|---|---|---|
| Thioanisole 2 | 124.2 | 31.3 g | 252 | 1.00 |
| Isobutyryl chloride | 106.6 | 29.0 g | 273 | 1.80 |
| Aluminum chloride (AlCl₃) | 133.3 | 34.5 g | 259 | 1.03 |
| o-Dichlorobenzene (ODCB) | | 160 mL | | |
| HCl | | 160 mL | | |

A slurry mixture of aluminum chloride (34.5 g, 259 mmol) in 100 mL of o-dichlorobenzene in a 500 mL reaction vessel, equipped with a thermocouple probe, reflux condenser, mechanical stirrer, nitrogen inlet adapter and an addition funnel, was cooled to 8° C. and isobutyryl chloride (29.0 g, 273 mmol) was added over 30 min while keeping the internal temperature at 10–15° C.

The addition of isobutyryl chloride is slightly exothermic and the reaction is cooled with an ice-water bath to maintain the batch temperature between 10–15° C.

The AlCl₃/isobutyryl choride complex in ODCB was aged at 5–10° C. for 30 min. Then, thioanisole 2 (31.3 g, 252 mmol) was added to the reaction mixture over 2 h while maintaining the internal temperature at 8–13° C. The addition of thioanisole is exothermic. Gaseous HCl is formed in the reaction. After 50% of the thioanisole is added, a precipitate is formed.

The reaction mixture was warmed to 12–16° C. over 1h and turned into a thick slurry. The progress of the reaction is monitored by HPLC analysis: 4.6×250 mm Inertsil ODS-2 column, Linear Gradient-70:30 to 20:80 Acetonitrile/20 mM aqueous $H_3PO_4$ over 20 min and hold for 5 min, 1.5 mL/min, column temp.=45° C., injection volume=20 mL, detection= 210 nm, sample preparation=500 X dilution.

The reaction mixture was cooled to 10° C. and 160 mL of 5% aqueous HCl were added over 45 min while keeping temperature at <20° C. The biphasic mixture was stirred for 1.0 h. The lower organic phase was removed. The aqueous phase was extracted with 20 mL ODCB. The combined ODCB solution was used directly for the next step. The yield of 3 is 95–98%.

Preparation of 4-Methylsulfonyl-isobutyrophenone 4

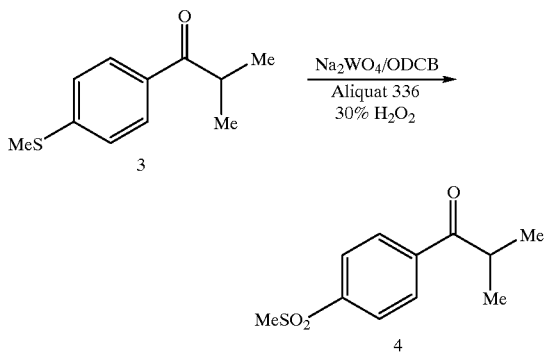

| Material | MW | amount | mmol | equiv. |
|---|---|---|---|---|
| 4-Thiomethyl-isobutyrophenone 3 (ODCB solution) | 194.4 | 48.8 g | 251 | 1.00 |
| Hydrogen peroxide, 30% (d = 1.11 g/mL) | 34 | 77.0 mL | 754 | 3.00 |
| Sodium tungstate dihydrate | 329.9 | 0.90 g | 2.73 | 0.01 |
| Aliquat 336 | 404 | 4.34 g | 10.7 | 0.04 |
| Water | 18.0 | 5.5 mL | | |
| Hexane | | 250 mL | | |

A solution of 4-thiomethyl-isobutyrophenone 3 (48.8 g, 2541 mmoL) in ODCB in 1.0 L reaction vessel, equipped with a thermocouple probe, reflux condenser, mechanical stirrer, nitrogen inlet adapter and addition funnel, was treated with a solution of $Na_2WO_4$ (0.9 g, 2.73 mmol) and Aliquat 336 (4.34 g, 10.7 mmoL) in water (5.5 mL). The heterogeneous mixture was heated with stirring at 35° C. and 6.0 mL of 30% $H_2O_2$ was added dropwise.

After the initial addition, the remaining $H_2O_2$ solution was added over 1 h while maintaining the temperature between 50–60° C. The reaction mixture was heated to 80° C., the lower organic phase was removed and cooled to room temperature and treated with hexane (250 mL) and seeded with keto-sulfone.

The solids were filtered and washed with 2×50 mL of hexanes. The product was dried in a vacuum oven at 25° C. to afford 46 g of the keto-sulfone 4 (98.5 A %, 81% yield from 3).

Preparation of the Enol Ether Epoxide 5

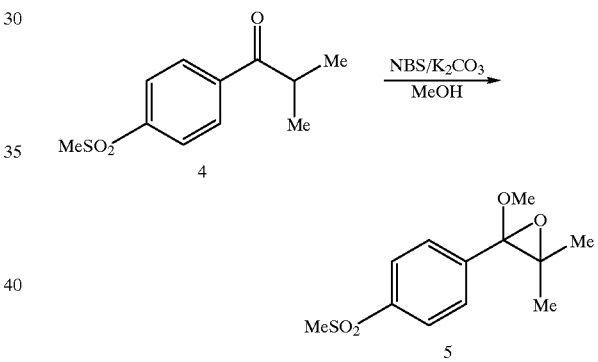

| Material | MW | amount | mmol | equiv. |
|---|---|---|---|---|
| 4-Methylsulfonyl-isobutryophenone 4 (ODCB solution) | 226.3 | 22.9 g | 101 | 1.0 |
| N-Bromosuccinimide (NBS) | 178.0 | 36.0 g | 202 | 2.0 |
| Potassium carbonate (K₂CO₃) | 138.2 | 22.0 g | 303 | 3.0 |
| MeOH | | 229 mL | | |
| 10% HCl | | 230 mL | | |
| Toluene | | 460 mL | | |
| 1N NaOH | | 230 mL | | |

To a 500 mL reaction vessel, equipped with a mechanical stirrer, nitrogen inlet adapter and thermocouple probe, was added 4-methylsulfonyl-isobutyrophenone 4 (22.9 g, 101 mmoL), N- bromo-succinimide (36.0 g, 202 mmol), and potassium carbonate (22.0 g, 303 mmol) in 229 mL of methanol. The resulting slurry was vigorously stirred at 25° C. for ~16 h.

The reaction mixture was cooled to 10° C. and 230 mL of 10% aqueous HCl was added over 5 min while keeping the temperature <20° C. Then, 460 mL of toluene was added and the biphasic mixture was vigorously stirred for 15 min. The toluene phase was removed and washed with 230 mL of 1N NaOH. The organic phase was removed and concentrated under reduced pressure and flushed with 200 mL of dry toluene and then concentrated under reduce pressure to yield epoxide 5 as a solid (25.25 g, HPLC purity of 97.2 A %) in 98% isolated yield.

The epoxide 5 was used directly for the next step without further purification.

Preparation of Ester 7

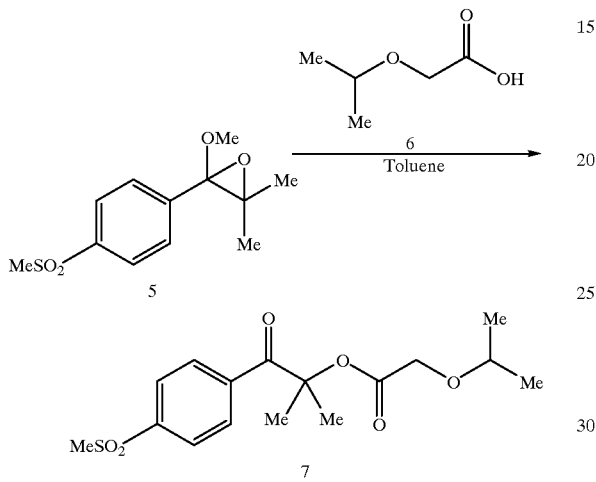

| Material | MW | amount | mmol | equiv. |
|---|---|---|---|---|
| Epoxide 5 | 256.3 | 21.0 g | 81.9 | 1.00 |
| Isopropoxyacetic acid 6 | 118.1 | 10.1 g | 85.5 | 1.04 |
| Toluene | | 210 mL | | |
| Ethanol | | 210 mL | | |

A solution of epoxide 5 (21.0 g, 81.9 mmol) and isopropoxyacetic acid 6 (10.1 g, 85.5 mmol) was dried via azeotropic distillation with toluene (2×250 mL) under reduced pressure. The reaction volume was adjusted to 210 mL. The solution is dried until the KF≦100 mg/mL The resulting dried solution was heated to 90° C. and aged for 2 h.

The reaction mixture was cooled to room temperature and the toluene was removed under reduced pressure. The resulting residue was dissolved in 210 mL of ethanol at 56° C. and then gradually cooled to 42° C. to precipitate the product. The resulting slurry was then cooled to room temperature and the product was collected by filtration and washed with 0–5° C. ethanol (20 ml) to afford crude ester 7 (~25 g)

The crude product was purified by recrystallization from ethanol (210 mL) at 60° C. and cooled to 58° C. and seeded with pure ester and slowly cooled to room temperature over 1.0 h. The slurry mixture was further cooled to 2° C. and the pure product was collected by filtration and washed with 60 mL of 0–5° C. cold ethanol. The product was dried in a vacuum oven at 25° C. to afford 19.5 g of the ester 7 in 70% yield with a HPLC A % purity of 99.4%.

Preparation of Compound 1

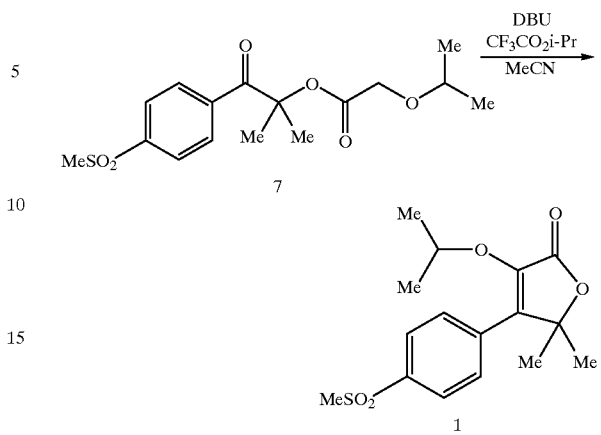

| Material | MW | amount | mmol | equiv. |
|---|---|---|---|---|
| Ester 7 | 342.4 | 15.2 g | 44.4 | 1.00 |
| DBU | 152.2 | 10.1 g | 66.6 | 1.50 |
| Isopropyl trifluoroacetate | 156.1 | 8.3 g | 53.3 | 1.20 |
| Acetonitrile | | 97 mL | | |
| Water | | 166 mL | | |

A 250 mL reaction vessel equipped with a mechanical stirrer, reflux condenser, nitrogen inlet, and thermocouple was sequentially charged with dry acetonitrile (97 mL, KF<100 mg/mL) isopropyl trifluoroacetate (8.3 g, 53.3 mmoL), and DBU (10.1 g, 66.6 mmol). The solution was stirred at 20° C. for 15 min and the ester 7 (15.2 g, 44.4 mmol) was added. The resulting solution was heated at reflux temperature under nitrogen for 18 h.

After the reaction was complete, the solution was cooled to ~40° C. and filtered through a glass fritted filter. The resulting filtrate was concentrated at 40–50° C. under reduced pressure until 70 mL of distillate was collected. Then, water (97 mL) was added slowly at 45° C. After 36 mL of water was added, the solution turned cloudy (40–45° C.) and 6 mg of crystalline Compound 1 was added as seed. The mixture was aged for 30 min and the remaining water (61 mL) was added. The mixture was cooled to 20° C. and aged at 20° C. for 6 h then filtered. The wet-cake was washed with 1:4 MeCN/water (2×10 mL). The product was air dried and dried at 35° C. under reduced pressure until constant weight to afford Compound 1 as a crystalline solid (12.9g, 89% isolated yield with a purity of >99.5 LCAP at 210 nm).

What is claimed:

1. A process for making compounds of Formula I

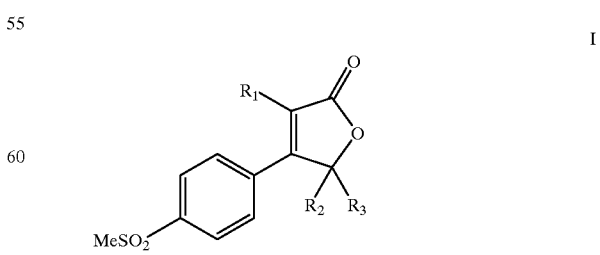

wherein $R_1$ is selected from the group consisting of (a) linear or branched $C_{1-6}$alkyl,
(b) linear or branched $C_{1-6}$alkoxy,
(c) mono-, di- or tri-substituted phenyl or naphthyl wherein the substituents are selected from the group consisting of
  (1) hydrogen,
  (2) halo,
  (3) $C_{1-3}$alkoxy,
  (4) CN,
  (5) $C_{1-3}$fluoroalkyl
  (6) $C_{1-3}$alkyl,
  (7) —$CO_2H$,
$R_2$ and $R_3$ are independently selected from the group consisting of
  (1) linear or branched $C_{1-6}$alkyl, or
  (2) aryl, optionally substituted with $R_1$,
$R_4$ is selected from the group consisting of
  (1) linear or branched $C_{1-6}$alkyl, or
  (2) aryl, optionally substituted with $R_1$,
comprising:

(a) reacting thioanisole of the formula

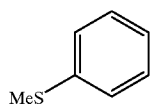

in a non-reactive solvent and in the presence of a Lewis Acid, with an acyl chloride

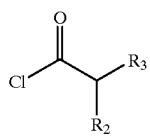

to yield compound III

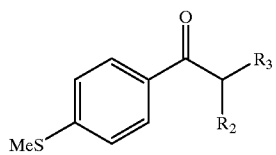

III (b) oxidizing compound III in a non-reactive solvent with an oxidizing agent, optionally in the presence of a suitable catalyst, to yield compound IV

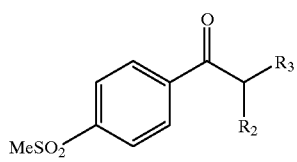

IV (c) reacting compound IV in an alkanol solvent with NBS and $K_2CO_3$ to yield the epoxide compound of formula V

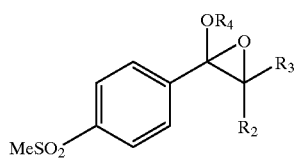

V (d) reacting compound V in a non-reactive solvent with an alkyl or alkoxyacetic acid VI

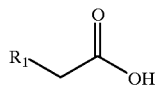

to yield a compound of formula VII

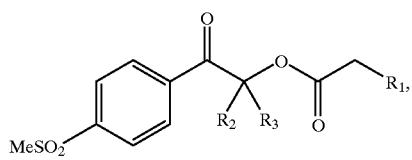

VII and (e) reacting compound VII in an aprotic solvent with a strong base and dehydrating in the presence of a water scavenger to yield a compound of formula I

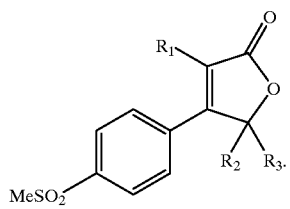

I

2. The process according to claim 1 wherein the water scavenger is isopropyl trifluoroacetate.

3. The process according to claim 1 wherein the aprotic solvent is acetonitrile.

4. The process according to claim 1 wherein the strong base is 1,8-diazabicyclo[5.4.0]undec-7-ene.

5. The process according to claim 1 wherein the water scavenger is isopropyl trifluoroacetate; the aprotic solvent is acetonitrile; and the strong base is 1,8-diazabicyclo[5.4.0] undec-7-ene.

6. The process according to claim 5 wherein $R_1$ is O—$CH(CH_3)_2$.

7. The process according to claim 5 wherein $R_2$ and $R_3$ are loweralkyl.

8. The process according to claim 7 wherein $R_2$ and $R_3$ are methyl.

9. A process for making compound 1 of the formula

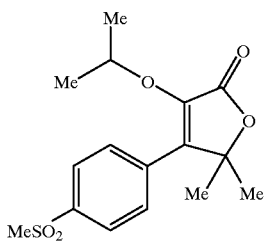

comprising (a) reacting thioanisole of the formula

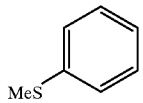

in a non-reactive solvent and in the presence of a Lewis Acid, with isobutyryl chloride

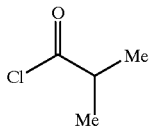

to yield compound 3

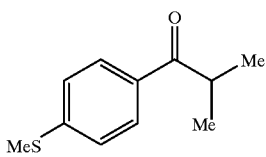

(b) oxidizing compound 3 in a non-reactive solvent with an oxidizing agent, optionally in the presence of a suitable catalyst, to yield compound 4

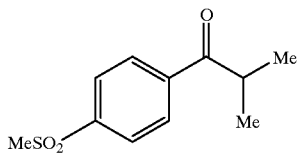

(c) reacting compound 4 in methanol with NBS and $K_2CO_3$ to yield the epoxide compound of formula 5

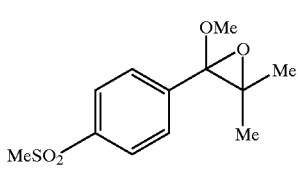

(d) reacting compound 5 in a non-reactive solvent with isopropoxyacetic acid 6

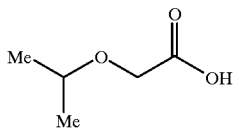

to yield a compound of formula 7

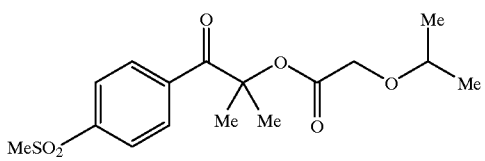

(e) reacting compound 7 in an aprotic solvent with a strong base and dehydrating in the presence of a water scavenger to yield Compound 1.

10. The process according to claim 9 wherein the water scavenger is isopropyl trifluoroacetate.

11. The process according to claim 9 wherein the aprotic solvent is acetonitrile.

12. The process according to claim 9 wherein the strong base is 1,8-diazabicyclo[5.4.0]undec-7-ene.

13. The process according to claim 9 wherein the water scavenger is isopropyl trifluoroacetate; the aprotic solvent is acetonitrile; and the strong base is 1,8-diazabicyclo[5.4.0]undec-7-ene.

14. A process for making compounds of Formula I

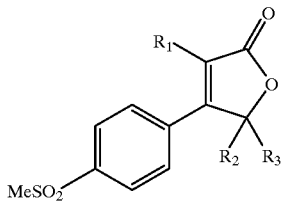

wherein $R_1$ is selected from the group consisting of
(a) linear or branched $C_{1-6}$alkyl,
(b) linear or branched $C_{1-6}$alkoxy,
(c) mono-, di- or tri-substituted phenyl or naphthyl wherein the substituents are selected from the group consisting of
(1) hydrogen,
(2) halo,
(3) $C_{1-3}$alkoxy,
(4) CN,
(5) $C_{1-3}$fluoroalkyl
(6) $C_{1-3}$alkyl,
(7) —$CO_2H$, $R_2$ and $R_3$ are independently selected from the group consisting of
(1) linear or branched $C_{1-6}$alkyl, or
(2) aryl, optionally substituted with $R_1$, $R_4$ is selected from the group consisting of
(1) linear or branched $C_{1-6}$alkyl, or
(2) aryl, optionally substituted with $R_1$ comprising the steps of (c) reacting compound IV of the formula

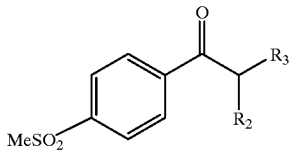

in an alkanol solvent with NBS and $K_2CO_3$ to yield the epoxide compound of formula V

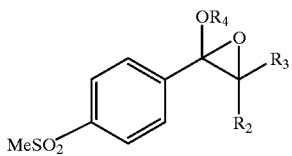

(d) reacting compound V in a non-reactive solvent with an alkyl or alkoxyacetic acid VI

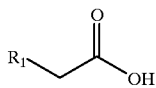

to yield a compound of formula VII

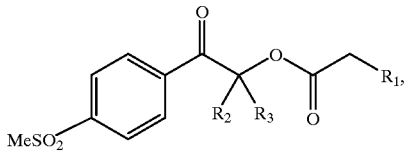

and (e) reacting compound VII in an aprotic solvent with a strong base and dehydrating in the presence of a water scavenger to yield a compound of formula I

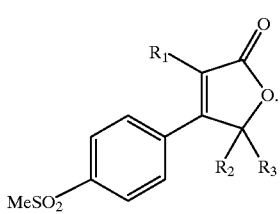

15. The process for making compound 1 of the formula

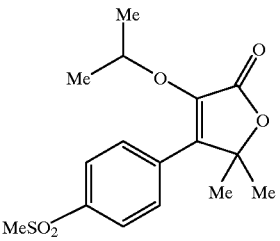

comprising the steps of (c) reacting compound 4 of the formula

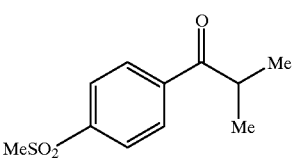

in methanol with NBS and $K_2CO_3$ to yield the epoxide compound of formula 5

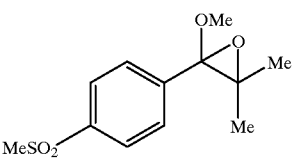

(d) reacting compound 5 in a non-reactive solvent with isopropoxyacetic acid 6

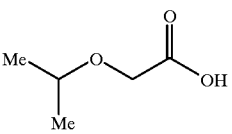

to yield a compound of formula 7

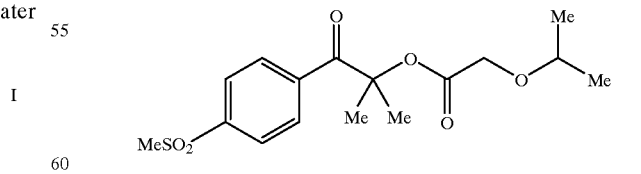

(e) reacting compound 7 in an aprotic solvent with a strong base and dehydrating in the presence of a water scavenger to yield Compound 1.

16. The process according to claim 14 for making compounds of Formula I, further comprising the step of:

(b) oxidizing compound III

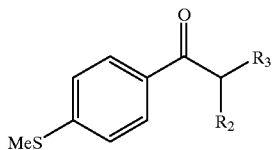

III in a non-reactive solvent with an oxidizing agent, optionally in the presence of a suitable catalyst, to yield compound IV.

17. The process according to claim 15 for making compound 1 further comprising the step of (b) oxidizing compound 3

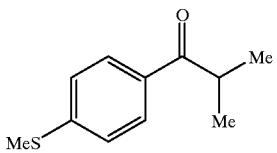

3 in a non-reactive solvent with an oxidizing agent, optionally in the presence of a suitable catalyst, to yield compound 4.

18. The process according to claim 14 wherein:
$R_1$ is O—CH(CH$_3$)$_2$, $R_2$ and $R_3$ are methyl, the water scavenger is isopropyl trifluoroacetate, the aprotic solvent is acetonitrile, and the strong base is 1,8-diazabicyclo[5.4.0]undec-7-ene.

* * * * *